US005888408A

United States Patent [19]

[11] Patent Number: 5,888,408

[45] **Date of Patent: *Mar. 30, 1999**

Nagels

[54] PROCESS FOR COLLECTING AND PREPARING STORED BLOOD, APPARATUS SUITABLE FOR SAID PROCESS AND USE OF THE APPARATUS

[75] Inventor: Hans-Otto Nagels, Bovenden, Germany

[73] Assignee: Heraeus Instruments GmbH & Co. KG, Hanau, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 676,312

[22] PCT Filed: Nov. 28, 1995

[86] PCT No.: PCT/EP95/04675

§ 371 Date: Sep. 9, 1996

§ 102(e) Date: Sep. 9, 1996

[87] PCT Pub. No.: WO96/17577

PCT Pub. Date: Jun. 13, 1996

[30] Foreign Application Priority Data

Dec. 8, 1994 [DE] Germany .......................... 44 43 577.0

[51] Int. Cl.$^{6}$ ......................... B01D 17/038; A61B 19/00; B65D 35/44

[52] U.S. Cl. ......................... 210/789; 210/94; 210/360.1; 222/93; 422/72; 436/177; 604/408; 604/410

[58] Field of Search .................................... 210/94, 360.1, 210/513, 541, 767, 782, 787, 789; 604/403, 408, 410, 4; 222/92, 94, 103; 422/101, 102, 72; 494/37; 383/37; 220/404; 436/177

[56] References Cited

U.S. PATENT DOCUMENTS

| | | | |
|---|---|---|---|
| Re. 33,924 | 5/1992 | Valeri | 604/408 |
| 3,087,491 | 4/1963 | Gewecke et al. | 220/404 |
| 3,847,738 | 11/1974 | Brake et al. | 604/403 |
| 4,869,398 | 9/1989 | Colvin et al. | 604/408 |
| 4,976,851 | 12/1990 | Tanokura et al. | 210/94 |
| 5,135,646 | 8/1992 | Tanokura et al. | 210/94 |
| 5,262,070 | 11/1993 | Ishida | 210/513 |
| 5,279,797 | 1/1994 | Burns et al. | 422/102 |
| 5,523,004 | 6/1996 | Tanokura et al. | 210/789 |
| 5,632,906 | 5/1997 | Ishida et al. | 210/782 |
| 5,674,441 | 10/1997 | Watanabe et al. | 422/101 |
| 5,690,248 | 11/1997 | Hulls | 220/404 |

*Primary Examiner*—Joseph W. Drodge

*Attorney, Agent, or Firm*—Workman, Nydegger & Seeley

[57] ABSTRACT

The invention is directed to methods and apparatus for collecting and preparing stored blood that minimizes handling and manipulation of blood bags to thereby reduce the contamination risk. In particular, the invention is directed to methods and apparatus wherein at least one sterilely packed blood bag is provided in a packaging apparatus that supports the blood bag during filling and also serves as the transport container for the blood bag. The packaging apparatus comprises a sterile package for at least one blood bag and has a completely enclosed interior space to hold the blood bag and a closure element used to open up the interior space. The interior space has a volume of at least 500 ml or can be expanded to at least 500 ml by applying an internal pressure directed outwards from the interior space and the interior space can be closed by the closure element. Preferably, the packaging apparatus also serves as a support during centrifugation of the collected blood.

18 Claims, 1 Drawing Sheet

PROCESS FOR COLLECTING AND PREPARING STORED BLOOD, APPARATUS SUITABLE FOR SAID PROCESS AND USE OF THE APPARATUS

BACKGROUND OF THE INVENTION

1. The Field of the Invention

The present invention relates to apparatus and processes for collecting and preparing stored blood, wherein at least one sterilely packed blood bag is disposed within a package where the blood bag can be filled with blood and then transported.

2. Present State of the Art

The collection of donated blood and the subsequent preparation of blood for storage are well known processes. Collected blood for transfusions is typically delivered in blood bag systems in which several blood bags are combined. For reasons of contamination, one preferably works in a closed system. For this purpose, all bags are equipped with interconnecting hose connections. In such a system, the so-called donor bag, the bag that contains the blood of the donor, can hold between 450 to 500 ml of blood; the other bags, which are designated as satellite bags, are either empty or filled with stabilizer solutions. For transport, for example to a blood donation site, the blood bag systems are each packed sterilely.

The packages for the new blood bags, or for the new blood bag systems, are made of tear-proof plastics. The packages and also the blood bags are disposable articles. To open the package, for example at a blood donation site, the package is torn open along a provided seam and the blood bag system is removed. This blood bag system can contain three to five blood bags. 450 to 500 ml of venous blood are then collected from the donor by means of an accompanying syringe. During this step, the blood bag system is located on a special rocker balance. The rocker balance controls the amount of blood collected and at the same time sets the maximum collection volume. In addition, to inspect the blood, a control tube containing blood is drawn out.

After the collection, all bags and hoses are packed in a special transport container. The blood is then transported to a blood bank in these transport containers where the stored blood is further prepared. The further preparation takes place, for example, by centrifugation. In this step, the blood bag systems are weighed and, in order to prevent undesired weights in the centrifuge, are tared against each other and then placed in special centrifuge inserts. After the centrifugation, the individual components of the respective blood bag systems are then separated.

The described method, beginning with the blood collection and extending to the separation of the individual components, is demanding in work and time. The blood bags and the hoses must be handled several times. For example, during packaging several persons unavoidably come in contact with the stored blood. Despite all precautions, this means an increased risk of contamination. The described tare procedure prior to the centrifugation also involves a great deal of work.

OBJECTS AND BRIEF SUMMARY OF THE INVENTION

The purpose of the present invention is therefore to provide a process that permits a simple and sterile collection and preparation of stored blood and to provide a suitable apparatus for this process. The apparatus makes possible handling of stored blood with low expenditure of work and low risk of contamination. In the present invention, a package used to store a blood bag system is also used as transport container. Since the package is used simultaneously as transport container, repackaging the blood bag or bags for transport is not necessary. The blood bag can also remain in the package during the blood collection. Removing the blood bag from the package is not necessary. One possible source of contamination is thereby eliminated. After the blood collection, if the desired amount of blood is contained in the blood bag, the package is closed. Repackaging in a special transport container is obviated. The blood can be transported in the package. An additional source of possible contamination is thereby eliminated.

In one embodiment, the inventive package can be used as a centrifuge insert. An additional source of possible contamination when repackaging the transport container into a conventional centrifuge insert is thereby obviated. Moreover, using the package as a centrifuge insert facilitates the handling during the preparation of stored blood. This is because insertion of blood bags into centrifuge inserts is very demanding. Secondly, elimination of conventional centrifuge inserts results in additional room for the blood bags to be centrifuged. This is very important for blood bag systems.

In another embodiment, the inventive package can also be inserted into the centrifuge insert. This step also eliminates a contamination source since the blood bag or bags do not need to be repackaged from the transport container to the centrifuge insert. Rather, the inventive package which serves as the transport container is inserted directly into the centrifuge insert.

With respect to the apparatus, volume of the interior space of the inventive package is at least 500 ml or is expandable to at least 500 mlThe expansion is produced by the application of an internal pressure that is directed from the interior space outward. The interior space can be closed by means of a closure device. The fact that the volume of the interior space is at least 500 ml or is expandable to at least 500 ml by the application of an internal pressure means that at least one blood bag having a blood volume of 450 to 500 ml can be received in the interior space. In addition to the donor blood bag, satellite bags can also be placed in the package. The minimum volume of the interior space must then be correspondingly greater or can be correspondingly further enlarged. The fact that the volume of the interior space of the package corresponds to at least that of a filled blood bag ensures that the blood bag or the blood bag system for collecting blood does not have to be removed from the package. The blood bag or bags remain inside the package during the collection until they contain the desired blood volume.

The application of internal pressure results from the fact that the blood bag gradually fills when the blood is collected. In so doing, the volume of the blood bag and the interior space of the package gradually increase. With a rigid package, the interior space can be adjusted, for example, to the typical shape of a filled blood bag. Inventive packages whose interior space volume is expandable have the advantage of occupying only a small space when the blood bag is empty. The packages with expandable interior space can be made, for example, from a flexible material and/or be provided with folded walls.

After the blood is collected, the package is closed. The package can be closed by means of a closure device. Removal of the blood bag or of a multiple blood bag system from the package is therefore not necessary while the blood is collected. This eliminates a possible contamination source. After the package is closed, the package is usable as a transport container for the collected stored blood. Repackaging in a special transport container is thus not necessary. Therefore, no persons come in contact with the blood bag or with the blood bag system for the repackaging. This also obviates a contamination source.

The inventive package also allows the centrifugation of the stored blood. For example, the package can be inserted either into a suitable centrifuge insert, or the package itself is constructed as a centrifuge insert. Removal of the blood bag or bags is not necessary in any case. Therefore, the inventive package eliminates possible contamination which could arise from manually moving the blood bag from a transport container to a centrifuge insert.

The closure device can have a closure to be opened only once, for example, a seam equipped with a pull-off lid. In this case, for subsequently closing the interior space, special closing parts, for example lids, are provided which function together with the package or with the blood bag. This ensures a closure of the interior space during transport. The inventive package can also be constructed for multiple use. In this case, the closure device has, for example, a zipper, a ziplock fastener, a push button, a turn fastener or another closing part for multiple use.

In inventive packages whose interior space has a volume of at least 1000 ml, or an interior space that is expandable to a volume of at least 1000 ml by application of internal pressure, have proven to be especially suitable. With such a package, even greater volumes of stored blood or blood bag systems are manageable from the blood collection to the centrifugation without repackaging of blood bags or hoses being necessary.

A package whose side walls are constructed in the shape of a bellows has proven to be especially suitable. Packages constructed in this manner facilitate an increase in the volume of the interior space when internal pressure is applied. When the blood is collected the internal pressure results from the gradual filling of the blood bag. Its increase in volume also gradually increases that of the interior space. The package occupies only a small space when the blood bag is empty; it therefore results in relatively low transport costs.

In one embodiment, the package is made essentially from an expandable plastic. Similar to the embodiment of the package in the shape of a bellows, in this embodiment the package yields when internal pressure is applied. Accordingly, during blood collection via the filling of the blood bag contained in the package, the interior space volume of the package gradually increases. In this process, the walls of the package bordering the interior space stretch. This embodiment has the additional advantage that the stretched walls exert a counterpressure on the blood bag inside the package and thereby also stabilize the blood bag in its respective position and arrangement.

An apparatus in which the package is made from a centrifugable plastic has proven to be especially favorable. This ensures that a repackaging of the blood bag or bags for the centrifugation is not necessary. It has also been proven favorable to construct the package from the same plastic as the blood bag. The plastics that are typically used for blood bags are centrifugable.

In one preferred embodiment of the apparatus, the closure device is constructed in the form of a lid connected to the package. On the free end of the lid a hollow space which is open on one side in the direction of the interior space. The hollow space on the lid is provided for receiving part of the blood bag. To transport the apparatus, the lid can be jammed between the inner wall of the package and the filled blood bag.

It has been proven to be advantageous to provide a display field for the weight class of the filled blood bag on the package. As described above, the blood bags or multiple blood bag systems are weighed on a rocker balance while the blood is collected. This weighing can also be applied to the total weight determination of package and inner contents. A display field is provided on a visible upper side of the package, to which display field a label can be attached. The weight class of the respective stored blood is indicated on the label. For example, weight classes of 5 g weight difference can be formed, whereby the weight classes can be indicated on the label either with numbers or letters or by means of a color code. For this purpose, the balance can print out a corresponding label, which is then adhered for example to the display field as a decal. This has the advantage that it does not have to be weighed and tared even once for the centrifugation of the stored blood, but can be inserted directly in the centrifuge according to its respective weight class. Instead of a color-coded label, other markers can also be used for the different weight classes, such as for example pull-off letters.

With respect to the use, to realize the above-mentioned purpose it is proposed that a sterile package for at least one blood bag be used. The package has an interior space enclosed on all sides for receiving the blood bag and a closure device for opening the interior space. The volume of the interior space is at least 500 ml or is expandable to at least 500 ml by the application of an internal pressure directed from the interior space outward. The interior space can be closed by means of the closure device for receiving at least one blood bag in the empty or filled state. The package can also function as a container for the centrifugation of the blood bag contents.

BRIEF DESCRIPTION OF THE DRAWING

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENT

Figure 1:
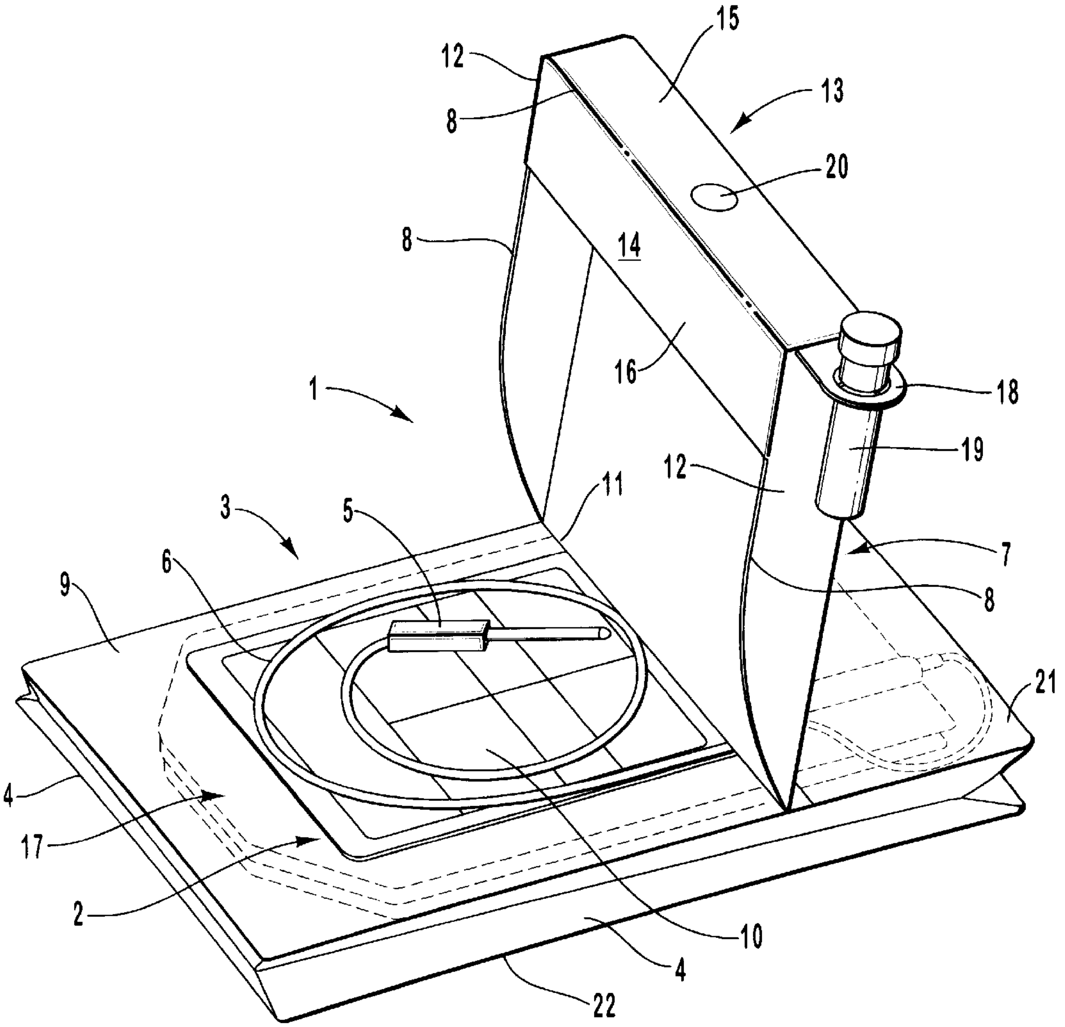
FIG. 1 is perspective view of a preferred embodiment of an apparatus in accordance with the present invention.

FIG. 1 shows a perspective top view of a preferred embodiment of an apparatus constructed for providing a blood bag system for use in collecting, transporting, and centrifuging blood.

The package 1 is designed for receiving the blood bag system 2 consisting of a donor bag and two satellite bags. In the FIGURE, the blood bag system 2 is depicted with dotted lines. The package 1 has a receiving chamber 3, in which the blood bag system 2 is stowed. The volume of the receiving chamber 3 can be modified depending on the volume that occupies the blood bag system 2. To increase the volume the side walls 4 of the receiving chamber 5 are folded in the shape of an accordion. If an internal pressure is applied, for example when the blood bag system 2 is filled during blood collection, the volume of the receiving chamber 3 increases corresponding to the increase in volume of the blood bag system 2. A syringe, which is indicated with reference number 5, serves to collect the blood. The syringe 5 is connected to a hose 6, which in turn is connected to the donor bag of the blood bag system 2.

The package 1 furthermore has a closure lid 7. In the delivery state, the blood bag system 2 is empty and unused. The closure lid 7 is connected to the receiving chamber 3 in such as manner that the interior space of the receiving chamber 3 is sterilely sealed. For opening the package 1, the connecting areas between the receiving chamber 3 and the closure lid 7 are in part constructed as target tear lines 8. Package 1 tears open along target tear lines 8 so as to form an aperture 9 when the closure lid 7 is pulled up. When the package 1 is opened, a label area 10 for receiving information on the stored blood is visible, in addition to the syringe 5 and the hose 6.

The closure lid 7 has in the top view of the package 1 essentially a right-angled cross section. With an edge serving as axis of rotation 11, the edge is also firmly connected to the receiving chamber 3 in the opened state and can be rotated around this axis 11. Starting from the target tear lines 8, the closure lid 7 is constructed with vertically spreading side parts 12. The side parts extend from the axis of rotation 11 up to the opposite free end 13 of the closure lid 7.

In the closed state of the package 1, the edges of the side parts 12 face in the direction of the receiving chamber 3 and are laminated with the upper side of the package 1. The target tear lines 8 run along the edges. The closure lid 7 is equipped at its free end 13 with a pocket 14 that is open on one side in the direction of the receiving chamber 3. The pocket 14 is bordered by the side parts 12 as well as by a front area 15 extending from the free end 13 of the closure lid 7 in the direction of the receiving chamber 3, and by a bottom area 16 running from the front area 15 essentially vertically in the direction of the axis of rotation 11. The pocket 14 serves to receive the end 17 of the blood bag system 2 facing it in the closed state of the package 1. The width of the pocket 14 determined by the side parts 12 is therefore greater than the corresponding dimension of the blood bag system 2 in this direction.

A holding tab 18 is provided on one of the side parts 12 of the closure lid 7 for holding a sample tube 19. The holding tab 18 encloses the sample tube 19. It is constructed in a perforated manner so that the sample tube 19 can be removed by tearing open the holding tab 18. On its front area 15 that faces up in the pulled-up state, the closure lid 7 is provided with a receiving area 19. The receiving area 19 serves for the attachment of an indication about the weight class of the package, including its contents.

The process in accordance with the invention is hereafter elucidated in more detail in an example with the embodiment of the apparatus in accordance with the invention shown in the FIGURE:

The blood bag system 2 is delivered sterilely packed in the package 1 to a blood donation site. The closure lid 7 is closely laminated with the receiving chamber 3. For the removal of the syringe 5, the closure lid is pulled open along the target tear lines 8. The blood bag system 2 remains in the receiving chamber 3.

During the blood collection, the donor bag of the blood bag system 2 is gradually filled. Due to the resulting increase in volume, the donor bag presses against the upper side 21 of the receiving chamber 3 and thereby causes the collapsible side walls 4 to yield. During the blood collection, the package 1 lies on a beam-type scale, not shown, with which the weight of the package has been tared prior to the beginning of the blood collection. The target weight of the stored blood to be collected is programmed into the scale. After the intended weight has been attained, the blood collection is automatically discontinued. The blood that is still present in the syringe and in the hose connection runs on into the donor bag. The scale indicates the actual attained weight of the stored blood. The weighing is also applied to determining the total weight of package, blood bag system, and stored blood. Corresponding to the attained total weight class, which is divided into 5 g gradations, a color-coded label is issued. The label is adhered to the receiving area 20 of the closure lid 7 for indexing the stored blood with regard to its weight class.

This classification facilitates the later centrifugation, since the stored blood will then not have to be weighed even once for taring the centrifuge for the centrifugation.

After the blood collection has ended, the blood bag system 2 is closed and the closure lid 7 is locked in place. In so doing, the end 13 of the blood bag system 2 located in the aperture 9 is inserted into the pocket 14 of the closure lid 7. Since the filled blood bag system 2 is jammed between the upper side of the receiving chamber 21 and the bottom side 22 of the package 2, the closure lid 7 that is in part inverted with its pocket 14 over the blood bag system 2 is also fixed to the blood bag system 2. The aperture 9 is thereby kept closed and the package 1 is suitable as a transport container, for example to a blood bank. Repackaging in a special transport container is not necessary. In the blood bank, the package 1 including the blood bag system 2 is centrifuged. For this purpose, the package 1 is used as a centrifuge insert just as it is. This is of great significance for multiple bag systems since the elimination of the centrifuge insert results in additional room for the bags and facilitates the handling, that is, the insertion of the bags into the carrier cup of the centrifuge. The data on the receiving area 20 of the closure lid 7 offers an additional facilitation for the centrifugation in that a single taring of the centrifuge is made possible without reweighing the stored blood bags.

What is claimed and desired to be secured by United States Letters Patent is:

1. Apparatus for collecting and preparing stored blood comprising:

(a) a package having a front wall, a back wall, and a pair of discrete expandable sidewalls extending therebetween, the package bounding a sterile interior space that communicates to the exterior through an opening;

(b) a blood bag disposed within the interior space, the blood bag bounding a sterile compartment configured to receive and retain blood, the sidewalls of the package being configured to expand under pressure produced by the blood bag as the blood bag is gradually filled with blood; and (c) a lid removeably positioned over the opening of the package to selectively enclose the blood bag within the package.

2. An apparatus as recited in claim 1, wherein the package is comprised of a centrifugal plastic.

3. An apparatus as recited in claim 1, wherein the interior space of the package is expandable to at least 500 ml.

4. An apparatus as recited in claim 1, wherein the discrete expandable sidewalls of the package are constructed in the shape of bellows.

5. An apparatus as recited in claim 1, wherein the package and the blood bag are comprised of the same material.

6. An apparatus as recited to claim 1, further comprising at least one additional blood bag disposed within the interior space of the package.

7. An apparatus as recited in claim 1, wherein the lid comprises a first end hingedly attached to the package and an opposing second end having a pocket formed thereat, the lid being operable between an open position wherein at least a portion of the blood bag is exposed to the opening in the package and a closed position wherein the lid substantially covers the opening and at least a portion of the blood bag within the interior space of the package is received within the pocket of the lid so as to secure the lid in the closed position.

8. Apparatus for collecting and preparing stored blood comprising:

(a) an expandable package bounding a sterile interior space that communicates to the exterior through an opening;

(b) a blood bag disposed within the interior space, the package being configured to expand under pressure produced by the blood bag as the blood bag is gradually filled with blood; and (c) a lid having a first end hingedly attached to the package and an opposing second end having a pocket formed thereat, the lid being operable between an open position wherein at least a portion of the blood bag is exposed to the opening in the package and a closed position wherein the lid substantially covers the opening and at least a portion of the blood bag within the interior space of the package is received within the pocket of the lid so as to secure the lid in the closed position.

9. An apparatus as recited in claim 8, further comprising a syringe attached to the blood bag.

10. An apparatus as recited in claim 8, further comprising at least a pair of satellite bags being fluidly coupled with the blood bag and disposed within the interior space of the package.

11. An apparatus as recited in claim 8, wherein the package is made of a stretchable plastic.

12. An apparatus as recited in claim 8, wherein the package is comprised of a centrifugable plastic.

13. An apparatus as recited in claim 8, wherein the interior space of the package is expandable to at least 1000 ml.

14. An apparatus as recited in claim 8, wherein the package further comprises a display field for a weight classification of the blood bag.

15. A method for collecting and preparing stored blood comprising:

(a) opening a lid on an package to at least partially expose a blood bag disposed within a sterile interior space of the package;

(b) drawing blood from a patient into the blood bag disposed within the package;

(c) transporting the package having the blood bag disposed therein to a blood preparation facility; and (d) inserting the package having the blood bag disposed therein into a centrifuge for separating the blood within the blood bag into discrete components.

16. A method as recited in claim 15, further comprising the step of after drawing the blood into the blood bag, closing the lid such that a portion of the blood bag is received within a pocket formed on the lid, the engagement of the blood bag within the pocket of the lid keeping the lid in the closed position.

17. Apparatus for collecting and preparing stored blood comprising:

(a) a package having a front wall, a back wall, and a pair of discrete sidewalls extending therebetween, at least one of the sidewalls including an expandable bellows, the package bounding an interior space communicating with the exterior through an opening;

(b) a blood bag disposed within the interior space of the package, the blood bag including a closed sterile compartment configured to receive and retain blood and a hose in fluid communication with the sterile compartment; and (c) a lid moveably positioned over the opening of the package to selectively enclose or access the blood bag within the package.

18. Apparatus for collecting and preparing stored blood comprising:

(a) an expandable package bounding an interior space that communicates to the exterior through an opening;

(b) a blood bag bounding a compartment configured to receive and retain blood disposed within the interior space of the package; and (c) a lid having a first end hingedly attached to the package and an opposing second end having a pocket formed thereat, the pocket being bounded by an encircling sidewall and having an access facing the first end of the lid, the lid being operable between an open position wherein at least a portion of the blood bag is exposed to the opening in the package and a closed position wherein the lid substantially covers the opening, the pocket being configured to receive at least a portion of the blood bag positioned within the interior space of the package when the lid is in the closed position.

* * * * *

UNITED STATES PATENT AND TRADEMARK OFFICE

CERTIFICATE OF CORRECTION

PATENT NO. : 5,888,408

DATED : Mar. 30, 1999

INVENTOR(S) : Hans-Otto Nagels

It is certified that error appears in the above-identified patent and that said Letters Patent is hereby corrected as shown below:

Col. 1, line 34, after "bags." change "450 to 500" to --Four hundred and fifty to five hundred--

Col. 2, line 2, after "contamination." insert a paragraph break

Col. 2, line 36, after "500" change "mlThe" to --ml. The--

Col. 5, line 1, after "volume" insert a comma

Col. 5, line 2, after "chamber" change "5" to --3--

Col. 5, line 13, after "such" change "as" to --a--

Col. 5, line 52, after both instances of "receiving area" change "19" to --20--

Col. 8, line 1, after "on" change "an" to --a--

Signed and Sealed this

Thirty-first Day of October, 2000

*Attest:*

Q. TODD DICKINSON

*Attesting Officer* — *Director of Patents and Trademarks*